United States Patent [19]

Heckele

[11] Patent Number: 5,411,507

[45] Date of Patent: May 2, 1995

[54] INSTRUMENT FOR IMPLANTING AND EXTRACTING STENTS

[75] Inventor: Helmut Heckele, Knittlingen, Germany

[73] Assignee: Richard Wolf GmbH, Knittlingen, Germany

[21] Appl. No.: 177,882

[22] Filed: Jan. 5, 1994

[30] Foreign Application Priority Data

Jan. 8, 1993 [DE] Germany .............. 43 00 285.4

[51] Int. Cl.⁶ .............................................. A61B 19/00
[52] U.S. Cl. .................................... 606/108; 606/198
[58] Field of Search ................. 128/20; 604/104–109; 606/1, 108, 190–199, 151, 213; 623/1, 11, 12, 900

[56] References Cited

U.S. PATENT DOCUMENTS

| | | | |
|---|---|---|---|
| 3,517,128 | 6/1970 | Hines | 606/198 |
| 3,557,794 | 1/1971 | Van Patten . | |
| 3,692,029 | 9/1972 | Adair | 604/105 |
| 4,250,873 | 2/1981 | Bonnet . | |
| 4,885,003 | 12/1989 | Hillstead | 604/107 |
| 4,921,484 | 5/1990 | Hillstead | 604/104 |
| 5,074,871 | 12/1991 | Groshong | 604/107 |
| 5,188,630 | 2/1993 | Christoudias | 606/191 |

FOREIGN PATENT DOCUMENTS

| | | |
|---|---|---|
| 0274846 | 7/1988 | European Pat. Off. . |
| 0364420 | 4/1990 | European Pat. Off. . |
| 835789 | 4/1952 | Germany . |
| 2238508 | 2/1973 | Germany . |
| 2550975 | 5/1976 | Germany . |
| 2611107 | 9/1977 | Germany . |
| 3518238 | 12/1985 | Germany . |
| 9207941 | 1/1993 | Germany . |
| 9205829 | 4/1992 | WIPO . |

*Primary Examiner*—Stephen C. Pellegrino
*Assistant Examiner*—Glenn Dawson
*Attorney, Agent, or Firm*—Panitch Schwarze Jacobs & Nadel

[57] ABSTRACT

An instrument is provided which is suitable, inter alia, for the implantation and extraction of stents in hollow body organs. The instrument has an inner first tube and an outer second tube that can be displaced axially relative to each other, and spreading elements that can be directed radially outwardly and flexibly from the longitudinal axis of the instrument for the purpose of holding the stent. The spreading elements can be brought into a position against the stent by means of a displacement of one of the tubes in one direction. The proximal and distal ends of the spreading elements are attached to respective rings which fix the spreading elements at a radial spacing from the longitudinal axis of the instrument. Through displacement of one of the tubes, which acts upon one of the rings, the distance between the rings can be changed, whereby upon reduction of this distance, the spreading elements are deformed, creating outwardly directed bows which exert force against the inner circumference of the stent.

11 Claims, 4 Drawing Sheets

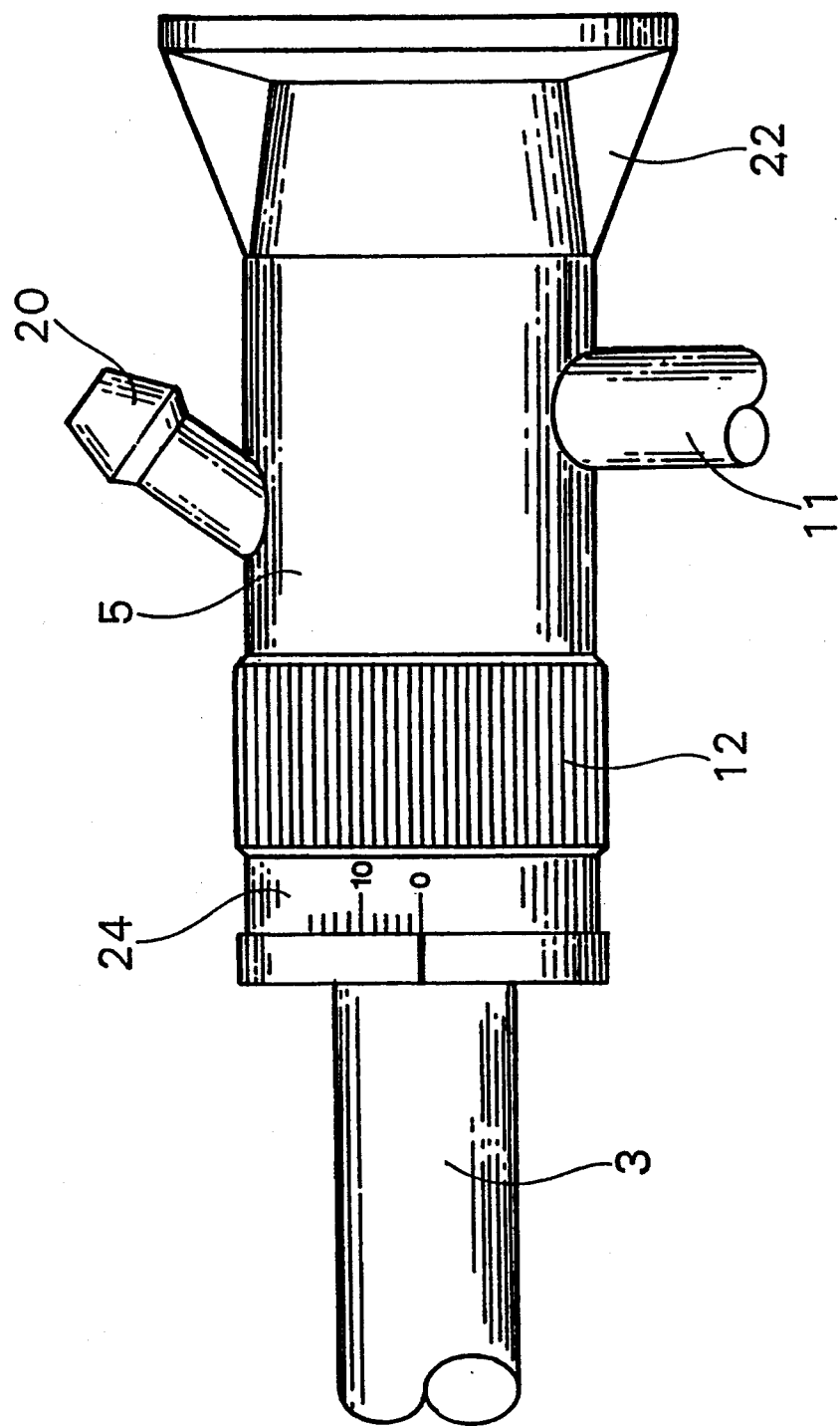

INSTRUMENT FOR IMPLANTING AND EXTRACTING STENTS

FIELD OF THE INVENTION

The invention is based on an instrument for implantation and extraction of stents for the re-channelization of hollow organs. The instrument comprises of an inner first tube and an outer second tube that can be displaced axially relative to the first, as well as spreading elements that can be directed radially outwardly and flexibly from the longitudinal axis of the instrument for the purpose of holding a stent, whereby the spreading elements can be brought into a position against the stent by moving the second tube in one direction.

BACKGROUND OF THE INVENTION

Tubular hollow organs bend as a result of pathological changes, which sometimes leads to occlusion or stenosis; such organs must be made passable once again. Various procedures are used for re-channelization, for example laser application, curettage, or the insertion of prostheses, which can be tubular for example and are then called stents. Problems often arise in the application of these stents, because the areas affected by stenosis lie very deep within the hollow organs, or else the organs have already become very severely deformed. Additional problems can arise due to the fact that a variety of sizes of these stents must be used, corresponding to the size of the hollow organ, and therefore the appropriate set of instruments must be available each time. Furthermore, it can become necessary to use an optic or to dispense gases or liquids during the positioning of the stent. Instruments are known for the application of such prostheses in a wide variety of forms, for example, from the following documents: U.S. Pat. No. 4,732,152; U.S. Pat. Nos. 4,848,343; 4,875,480; 4,533,545; 4,771,773; DE-OS 35 18 238; DE-OS 37 04 094; DE-OS 36 40 745; and DE-OS 33 22 001.

In addition, instruments are also known that are either provided with a balloon for the expansion of the hollow organ and setting a stent or are configured as a tube without additional spreading elements. While with balloons it is often disadvantageous that they are very easily deformable and are generally less suited to the application of tubular stents, tubular instruments make necessary the use of additional instruments, such as forceps and the like for application of the stent. An extraction of stents is not possible with these instruments.

From EP-A1 0 364 420 another instrument is known with which it is possible to transluminally implant or extract an essentially tubular and radially expandable stent. With this instrument the object of being able to exactly place and, equally exactly, to extract a stent is solved, whereby both procedures can be performed under observation through use of an optic. This instrument comprises essentially of an inner tube which is surrounded by a second tube that can be moved relative to the inner tube. In addition, a number of spreading elements are arranged on the inner tube, by means of which a stent can be held on the instrument and can be brought to the site of the application. When the outer tube is pushed back, the stent is brought under the influence of the spreading elements, which protrude radially outward. By means of a forward push on the outer tube, the spreading elements are pressed radially inward, whereby the stent is held firmly by the spreading elements between the inner and outer tubes. Then, under observation with the aid of an optic, the stent is brought to the site of treatment and is placed there when the above-described procedure for gripping the stent is carried out in reverse. Finally, the instrument is again withdrawn from the body cavity. With this instrument the space between the inner and outer tubes can also be used to introduce a liquid into the body cavity in order to rinse the distal end of the endoscope optic for a better view. In the same way, stents can be removed with this instrument under observation, whereby the operation described above is carried out in reverse order.

This instrument does not include any means of its own for the illumination of the body cavity, and can therefore be used only in conjunction with an endoscope, for example, a bronchoscope. This instrument also has the serious disadvantage that the free ends of the spreading elements can stick in the surrounding tissue, which can lead to serious injury to the hollow organ, for example, during bronchoscopy of the trachea and bronchial tubes. The fact that the stent cannot be applied correctly for some uses turns out to be an additional disadvantage. Similar problems also arise for instruments such as those disclosed in DE-G 92 07 941.

It is an object of the invention to provide an instrument with which stents can be correctly placed in a simple manner into tubular, hollow organs of various sizes, and just as easily removed from the body cavity again, and specifically, in such a way that any damage to the surrounding tissue that is caused by the mechanism for application of the stent is avoided, and that in addition, the otherwise common endoscopic treatments of hollow organs with auxiliary instruments and rinsing fluids can be carried out as well.

SUMMARY OF THE INVENTION

In accordance with the invention, the above objects are achieved with an instrument of the above-described type, but wherein both the proximal and distal ends of the spreading elements are attached to a respective ring, and are fixed with regard to their radial spacing from the longitudinal axis of the instrument. Through displacement of the second tube, which acts upon one of the rings, the distance between the rings can be varied, and the spreading elements can thus be deformed, creating outwardly directed bows which can be brought into a position which exerts force against the inner circumference of the stent.

The decisive advantage of an instrument configured in such a way is that by securing both the proximal and distal ends of the spreading elements within the periphery of the outer tube, free ends are avoided that could otherwise lead to injuries during introduction of the instrument into, or its removal from, a hollow organ that is to be re-channelized. In addition, the force necessary for holding and deforming the stent can be precisely adjusted to each individual need by axially displacing the second tube to a greater or lesser extent.

In accordance with a preferred embodiment of the instrument according to the invention, the inner tube has at its distal end region an enlargement, the outer diameter of which corresponds to that of the outer tube and the rings. The instrument thus has a spreading device integrated therein without presenting an exterior step.

Through the placement of washers made of low-friction material between the respective rings and the proximal face of the enlargement and the distal face of the outer tube, the inner tube of the instrument can be turned easily relative to the spreading device and thus to the stent as well. Because of this, during the placing of the stent in the hollow organ it is, for example, possible to check the exact positioning of the stent from a number of different viewing angles by means of an optic introduced into the inner tube.

One advantageous embodiment of the spreading device results when the spreading elements are formed as leaf springs made from strips of spring material, and each of their proximal and distal attachments to the rings is implemented by means of a joint that allows for a bow-like expansion of the leaf springs (i.e., convex) relative to the rings and tubes. When this is done, an attachment of the spreading elements to the rings by means of joint axles, each of which lies inside the outer diameter of the rings, results in a preferred device for the expansion of the spreading elements when the rings are pushed towards each other, an expansion that is directed radially outwardly.

The inner tube can be made attachable at its proximal end to a receiving part that allows for the introduction of fluids through the cavity of the inner tube and into the hollow organ. This part is provided with a connection for introducing the optic into the cavity of the tube. With this it is possible to check the position of the stent and, if necessary, for example in the case of branching hollow organs, to examine a branch and locate the exact location at which the stent must be applied.

For reasons of expediency, the receiving part can also be equipped with an adjustment mechanism for the axial displacement of the outer tube relative to the inner tube. This mechanism can comprise an adjusting nut that stands in a working relationship with the proximal end of the outer tube. For checking the extent of displacement of the two tubes relative to each other, that is, the degree of bowing outward of the spreading elements of the spreading mechanism as well, the outer tube can be equipped with a scale in the region of the adjusting nut, which also makes it possible to reproduce adjustments that have been previously determined to be favorable.

Finally, a fiber-optic light guide can be fixed inside the cavity of the inner tube for illumination of the area of activity. The light guide can run from the distal end of the tube to a light-guide cable attachment piece located in the proximal end receiving part.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings, like numerals are used to indicate like elements throughout.

FIG. 9 is a side view of the proximal end of the instrument illustrating the adjusting nut and scale.

DETAILED DESCRIPTION OF THE PREFERRED EMBODIMENT

Figure 1:
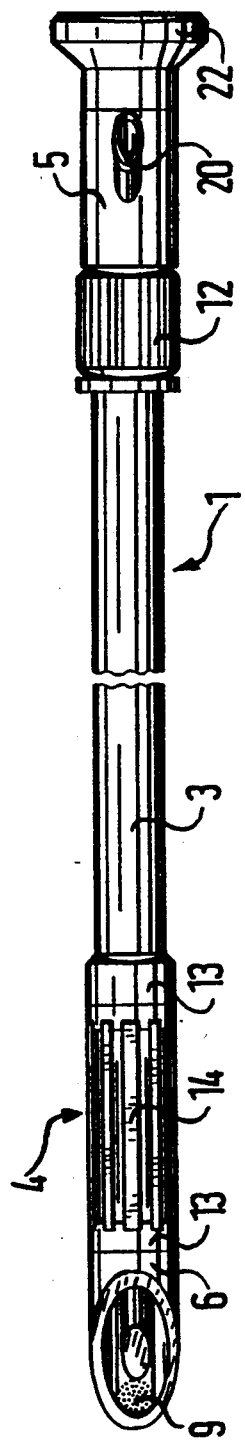
FIG. 1 is an overall view of the instrument.
Figure 2:
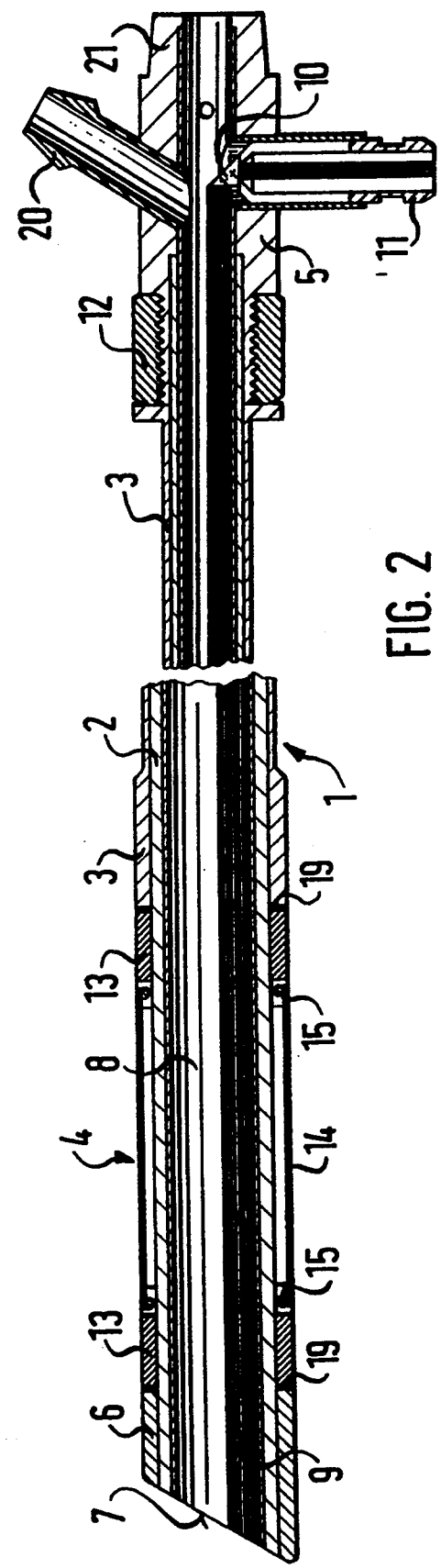
FIG. 2 shows the instrument according to FIG. 1 in longitudinal section and partially enlarged.

In accordance with FIGS. 1 and 2, the instrument 1 comprises essentially an inner tube 2 and a tube 3 that can be turned and axially displaced relative to tube 2 and can optionally be locked into position, a spreading device 4 in the distal region, and a receiving part 5 at the proximal end of the instrument.

The inner tube 2 is detachably seated with its proximal end in the receiving part 5 and is distally provided with an enlargement 6 that ends in an oblique section 7. In the cavity 8 of the inner tube 2 there is also fixed a bundle of fiber-optic light guides 9 that end proximally at a prism 10. A light-guide cable attachment piece 11 is included in the receiving part 5. The light guides 9 terminate distally with the inner tube 2.

Figure 3:
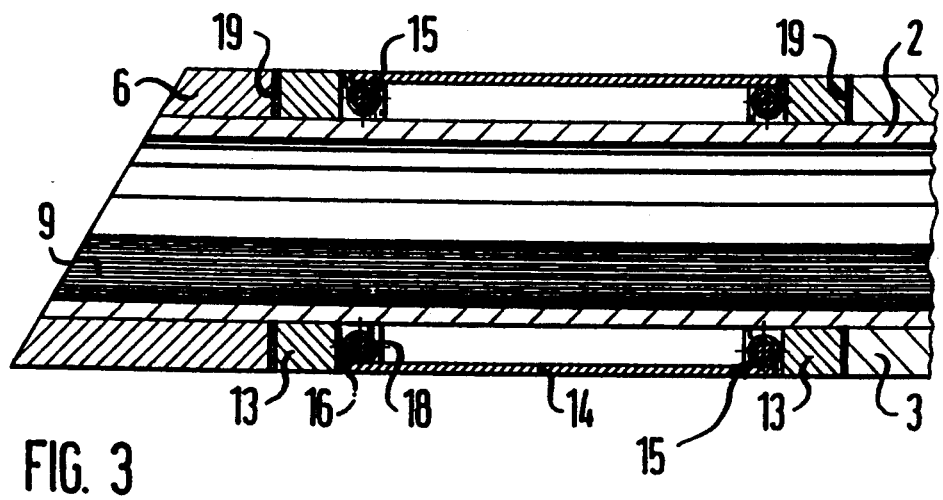
FIG. 3 is an enlarged longitudinal sectional view of the distal region of the instrument.
Figure 4:
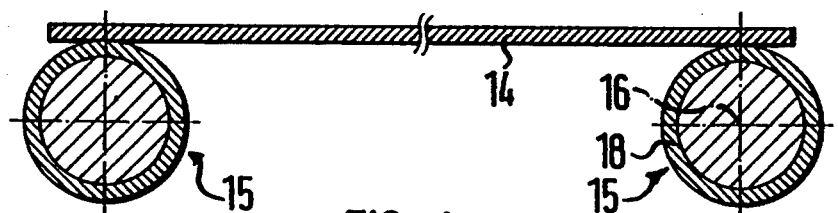
FIG. 4 is an enlarged detail section view of a spreading element.
Figure 6:
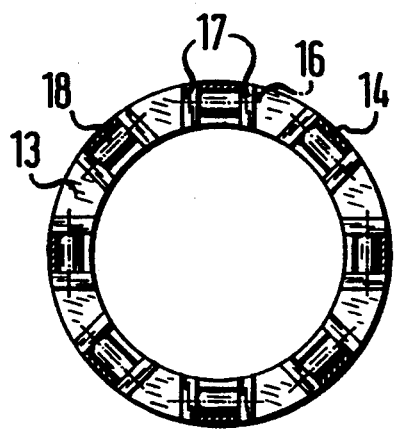
FIG. 6 is a front view of the embodiment shown in FIG. 5.
Figure 5:
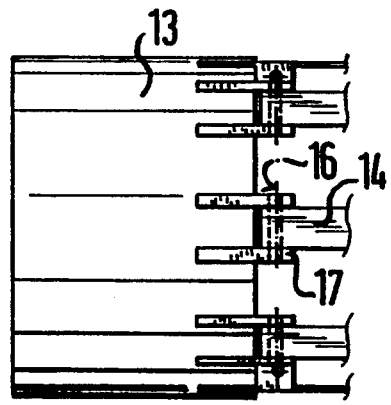
FIG. 5 shows one ring of the spreading device with coupled spreading elements.

The outer tube 3 is positioned on the inner tube 2 in a freely movable fashion and at its proximal end abuts against an adjusting nut 12. The outer tube 3 is shorter than the inner tube 2, so that a free space is formed between the proximal face of the enlargement 6 and the distal face of the outer tube 3. The spreading device 4 is arranged in this free space (see also FIG. 3). It comprises two rings 13 that are slidably guided on the inner tube 2 and are linked with each other by means of spreading elements 14. The spreading elements 14 are formed as leaf springs made from strips of spring material, and are connected at their ends to the rings 13 by means of joints, whereby a multi-bladed tubular body is formed. Each of the joints 15 is formed in accordance with FIGS. 4, 5, and 6 by means of a joint axle 16, which passes through a fork head 17 that projects from the face of each ring. Around each joint axle 16 there is a tube 18, on whose surface shell the end of one of the mentioned leaf springs is tangentially attached in a suitable fashion by, for example, cementing, soldering, or welding.

Each of the rings 13 abuts at its free face against washers 19 that are made of a low-friction material and are placed between the respective rings 13 and the proximal end face of the enlargement 6 and the distal end face of the outer tube 3.

As can be further seen, particularly in FIG. 2, the receiving part has an additional connecting sleeve 20 connected with the cavity 8 of the inner tube 2 and used for conducting fluids through the cavity 8 and into the hollow organ. In addition, a connection 21 is provided, on which can be detachably mounted an optic 22 that can be guided through the cavity 8 of the inner tube 2. Auxiliary instruments and the mentioned fluids can be conducted through the remaining free space between the inner tube 2 and the optic 22.

Figure 8:
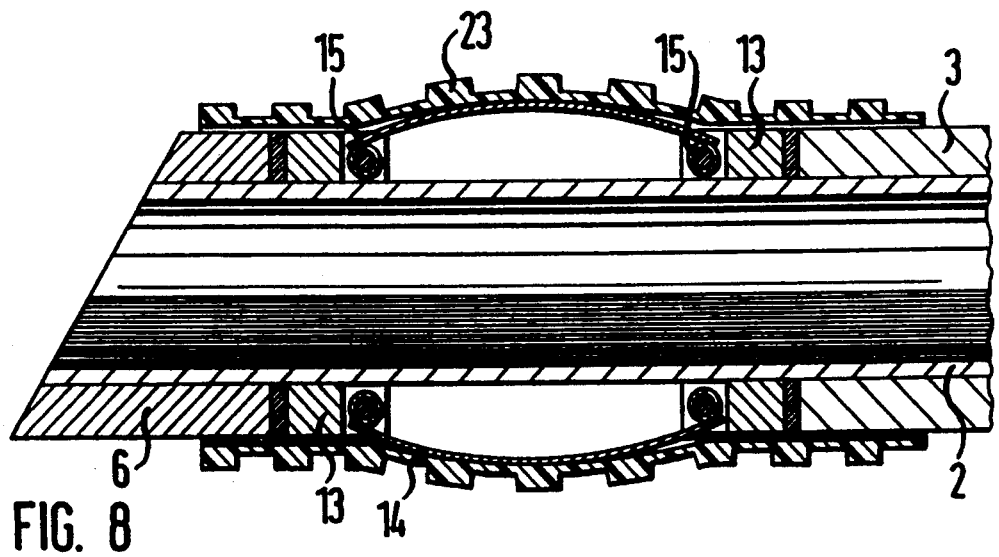
FIG. 8 is a representation corresponding to FIG. 7 with a stent in expanded position.
Figure 7:
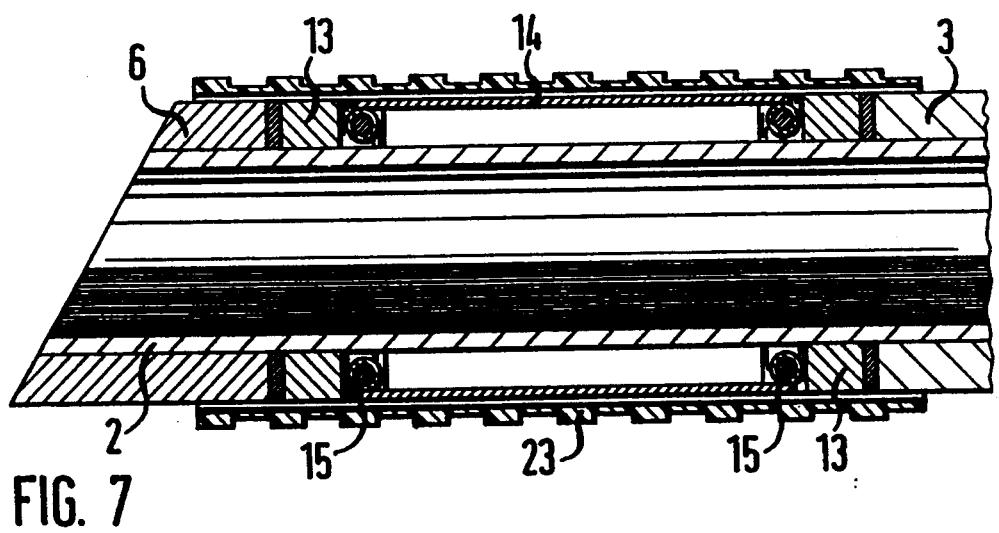
FIG. 7 is a representation corresponding to FIG. 3 with a stent surrounding the spreading device.

The following procedure is used in the application of the instrument 1 in accordance with the invention: A fit-selected stent 23 that is to be inserted into a hollow organ is first pushed over the enlargement 6 of the inner tube 2 until it is all the way over the spreading elements 14 (FIG. 7). The outer tube 3 is then pushed forward on the inner tube 2 in a distal direction by turning adjusting nut 12, whereby the distance between the rings 13 is narrowed with the result that the spreading elements 14 bow radially outwardly and come into a position which exerts force against the inner surface of the stent (FIG. 8). In this way the stent 23 that encircles the spreading elements 14 is secured to the instrument 1. Then, using visual observation by means of the optic 22, the instrument 1 with the stent is introduced into the hollow organ, and the stent is brought to the site to be treated. There the spreading elements 14 are returned to their resting positions by appropriate turning of the adjusting nut 12 in the reverse direction, so that the instrument 1 can be withdrawn from the placed stent, while the stent remains at the treatment site.

For this procedure, it proves to be advantageous that the inner tube 2 can be turned with respect to the stent 23, since it is thereby possible to check the seating of the stent 23 by looking from a variety of viewing angles, and to correct the placement of the stent by means of renewed engagement with the instrument.

With the instrument 1 in accordance with the invention, the removal of a stent 23 is, of course, possible as well. To do so, it is only necessary to reverse the procedure described above.

The strength of spreading of the spreading elements 14 can be monitored by means of a scale 24, as shown in FIG. 9 that indicates the extent of movement of the outer tube 3 and therefore the amount of spread of the spreading elements as well. In this way the danger of the hollow organ and the stent 23 itself being over-expanded can be practically eliminated.

The described displacement of the outer tube relative to the inner one can be resolved especially easily in terms of design. With regard to the functioning of the instrument, one can, however, achieve the same results if the inner tube is movable relative to a stationary outer tube.

In addition, the instrument can also be used for other purposes, that is not just for the implantation and extraction of stents. Thus it is possible, for example, to widen hollow organs and body channels with the spreading elements, to correct stenoses, or to raise organs and tissue, such as the abdominal wall, or hold them away from a location in the body at which a diagnosis or therapeutic measure is to be carried out.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An instrument (1) for implanting and extraction of stents for the re-channelization of hollow organs, comprising an inner first tube (2) and an outer second tube (3) which slidably houses and is axially displaceable relative to the first tube, said first and second tubes having a common longitudinal axis and respective proximal and distal ends, spreading elements (14) that can be directed radially outwardly and flexibly from said longitudinal axis for the purpose of holding a stent, whereby the spreading elements (14) can be brought into a position against an inner surface of a stent by means of axial movement of one of said tubes, the spreading elements (14) having proximal and distal ends each attached to a ring (13) and being secured with regard to their radial spacing from the longitudinal axis, each of said rings (13) slidably engaging said first tube (2), whereby through displacement of one of said tubes, which acts upon one of the rings (13), the distance between the rings (13) is varied and the spreading elements (14) are thereby deformed, thus creating in said spreading elements radially outwardly expanding bows which exert force against the inner surface of a stent, wherein the rings (13) are carried on the inner tube (2) in such a way that they can be turned freely on the inner tube, and an outer diameter of the rings corresponds to an outer diameter of the outer tube (3), and further comprising washers (19) made of low-friction material, which are placed between the respective rings (13) and a proximal end face of a distal enlargement on the inner tube (6) and the distal end of the outer tube.

2. An instrument according to claim 1, wherein the distal enlargement (6) has an outer diameter that corresponds to the outer diameter of the outer tube (3), and the rings (13) are located between the enlargement (6) and the distal end of the outer tube (3).

3. An instrument (1) for implanting and extraction of stents for the re-channelization of hollow organs, comprising an inner first tube (2) and an outer second tube (3) which slidably houses and is axially displaceable relative to the first tube, said first and second tubes having a common longitudinal axis and respective proximal and distal ends, spreading elements (14) that can be directed radially outwardly and flexibly from said longitudinal axis for the purpose of holding a stent, whereby the spreading elements (14) can be brought into a position against an inner surface of a stent by means of axial movement of one of said tubes, the spreading elements (14) having proximal and distal ends each attached to a ring (13) and being secured with regard to their radial spacing from the longitudinal axis, each of said rings (13) slidably engaging said first tube (2), whereby through displacement of one of said tubes, which acts upon one of the rings (13), the distance between the rings (13) is varied and the spreading elements (14) are thereby deformed, thus creating in said spreading elements radially outwardly expanding bows which exert force against the inner surface of a stent, wherein the spreading elements (14) comprise leaf springs made from strips of spring material, and each of their proximal and distal attachments to the rings (13) comprises a tangential joint (15) that allows for a bow-like expansion of the spreading elements relative to the rings (13) and tubes.

4. An instrument according to claim 3, wherein the spreading elements (14) together with the rings (13) form a multi-blade tube, having an outer diameter which corresponds to both an outer diameter of the outer tube (3) and an enlargement (6) of the distal end of the inner tube (2).

5. An instrument according to claim 4, wherein each joint (15) has an axle (16) lying radially inwardly of the outer diameter of the multi-blade tube.

6. An instrument (1) for implanting and extraction of stents for the re-channelization of hollow organs, comprising an inner first tube (2) and an outer second tube (3) which slidably houses and is axially displaceable relative to the first tube, said first and second tubes having a common longitudinal axis and respective proximal and distal ends, spreading elements (14) that can be directed radially outwardly and flexibly from said longitudinal axis for the purpose of holding a stent, whereby the spreading elements (14) can be brought into a position against an inner surface of a stent by means of axial movement of one of said tubes, the spreading elements (14) having proximal and distal ends each attached to a ring (13) and being secured with regard to their radial spacing from the longitudinal axis, each of said rings (13) slidably engaging on said first tube (2), whereby through displacement of one of said tubes, which acts upon one of the rings (13), the distance between the rings (13) is varied and the spreading elements (14) are thereby deformed, thus creating in said spreading elements radially outwardly expanding bows which exert force against the inner surface of a stent, and a receiving part (5) into which the proximal end of the inner tube is attached, the receiving part (5) having a connection (21) for attaching an optic thereto for removably introducing said optic (22) into a cavity (8) of the inner tube (2).

7. An instrument according to claim 6, wherein the receiving part (5) has at least one connecting sleeve (20) for the introduction of fluids into the cavity (8) of the inner tube (2).

8. An instrument according to claim 6, wherein the inner tube (2) includes means for releasably attaching the inner tube to the receiving part (5).

9. An instrument (1) for implanting and extraction of stents for the re-channelization of hollow organs, comprising an inner first tube (2) and an outer second tube (3) which slidably houses and is axially displaceable relative to the first tube, said first and second tubes having a common longitudinal axis and respective proximal and distal ends, spreading elements (14) that can be directed radially outwardly and flexibly from said longitudinal axis for the purpose of holding a stent, whereby the spreading elements (14) can be brought into a position against an inner surface of a stent by means of axial movement of one of said tubes, the spreading elements (14) having proximal and distal ends each attached to a ring (13) and being secured with regard to their radial spacing from the longitudinal axis, each of said rings (13) slidably engaging on said first tube (2), whereby through displacement of one of said tubes, which acts upon one of the rings (13), the distance between the rings (13) is varied and the spreading elements (14) are thereby deformed, thus creating in said spreading elements radially outwardly expanding bows which exert force against the inner surface of a stent, and an adjusting nut (12) for effecting the axial displacement of the tubes (2, 3) relative to each other, said adjusting nut (12) being located at the proximal end of the outer tube (3).

10. An instrument according to claim 9, further comprising a scale provided adjacent to the adjusting nut (12) for indicating the extent of axial displacement of the tubes.

11. An instrument (1) for implanting and extraction of stents for the re-channelization of hollow organs, comprising an inner first tube (2) and an outer second tube (3) which slidably houses and is axially displaceable relative to the first tube, said first and second tubes having a common longitudinal axis and respective proximal and distal ends, spreading elements (14) that can be directed radially outwardly and flexibly from said longitudinal axis for the purpose of holding a stent, whereby the spreading elements (14) can be brought into a position against an inner surface of a stent by means of axial movement of one of said tubes, the spreading elements (14) having proximal and distal ends each attached to a ring (13) and being secured with regard to their radial spacing from the longitudinal axis, each of said rings (13) slidably engaging on said first tube (2), whereby through displacement of one of said tubes, which slides one of the rings (13), the distance between the rings (13) along said inner tube is varied and the spreading elements (14) are thereby deformed, thus creating in said spreading elements radially outwardly expanding bows which exert force against the inner surface of a stent, wherein the inner tube (2) has a longitudinal cavity (8) in which is fixed a fiber-optic light guide (9), said light guide extending from the distal end of the inner tube (2) to a light-guide cable connector (11) located in a receiving part (5) at the proximal end of the inner tube (2).

* * * * *